United States Patent [19]
Walker et al.

[11] Patent Number: 6,027,461
[45] Date of Patent: Feb. 22, 2000

[54] INFUSION GUIDEWIRE HAVING FIXED CORE WIRE AND FLEXIBLE RADIOPAQUE MARKER

[75] Inventors: Blair D. Walker, Long Beach; Scott M. Evans, Santa Ana, both of Calif.

[73] Assignee: Micro Therapeutics, Inc., Irvine, Calif.

[21] Appl. No.: 08/541,147

[22] Filed: Oct. 11, 1995

[51] Int. Cl.$^7$ ...................................................... A61B 5/00
[52] U.S. Cl. ............................. 600/585; 604/96; 604/280
[58] Field of Search ................................... 600/585, 433, 600/434; 604/280, 281, 282

[56] References Cited

U.S. PATENT DOCUMENTS

| | | | |
|---|---|---|---|
| 3,841,308 | 10/1974 | Tate | 128/2 |
| 4,464,176 | 8/1984 | Wijayrathna | 604/164 |
| 4,538,622 | 9/1985 | Samson et al. | 128/772 |
| 4,748,986 | 6/1988 | Morrison et al. | 128/772 |
| 4,917,104 | 4/1990 | Rebell | 128/772 |
| 4,922,924 | 5/1990 | Gambale et al. | 600/585 |
| 4,932,419 | 6/1990 | de Toledo | 128/772 |
| 4,955,862 | 9/1990 | Sepetka | 604/164 |
| 5,174,302 | 12/1992 | Palmer | 128/772 |
| 5,178,158 | 1/1993 | de Toledo | 128/772 |
| 5,184,627 | 2/1993 | de Toledo | 128/772 |
| 5,211,636 | 5/1993 | Mische | 604/264 |
| 5,322,508 | 6/1994 | Viera | 604/52 |
| 5,554,114 | 9/1996 | Wallace et al. | 604/53 |
| 5,569,197 | 10/1996 | Helmus et al. | 604/96 |
| 5,624,396 | 4/1997 | McNamara et al. | 604/93 |
| 5,626,564 | 5/1997 | Zhan et al. | 604/164 |
| 5,640,970 | 6/1997 | Arenas | 600/585 |

OTHER PUBLICATIONS

"Products for Regional Thrombosis" brochure of Meditech (Boston Scientific Corp.) 1992 (7 pages).

T. McNamara M.D. et al., "Coaxial system improves thrombolysis of ischemia", Diagnostic Imaging, pp. 122–131, Nov. 1991.

*Primary Examiner*—Cary O'Connor
*Assistant Examiner*—Pamela L. Wingood
*Attorney, Agent, or Firm*—Joseph F. Breimayer

[57] ABSTRACT

An infusion guidewire that can be used either as a guidewire or an infusion catheter having an integral, tapered core wire within an infusion lumen formed of the aligned lumens of the conduit of a proximal connector housing, a proximal inner sheath in a proximal guidewire portion and a distal coil wire in a distal guidewire portion. The core wire proximal end is attached to the connector housing, and the core wire distal end is connected to the distal end of the distal wire coil. An outer sheath is attached to the connector housing and formed over the proximal inner sheath and the distal wire coil. A plurality of infusion side holes are formed in a distal infusion segment of the outer sheath in fluid communication with the infusion lumen. At the junction of the proximal inner sheath and the distal wire coil, a radiopaque wire coil of a material having a higher radiopacity than the distal wire coil is formed into a plurality of radiopaque wire coil turns of substantially the same pitch, inner lumen diameter and outer diameter as the distal wire coil. The radiopaque wire coil turns are wound into spacings between adjacent turns of the proximal wire coil such that the wire coils and the inner coil lumens are substantially co-axially aligned and maintained in alignment by the inner and outer sheathes.

15 Claims, 2 Drawing Sheets

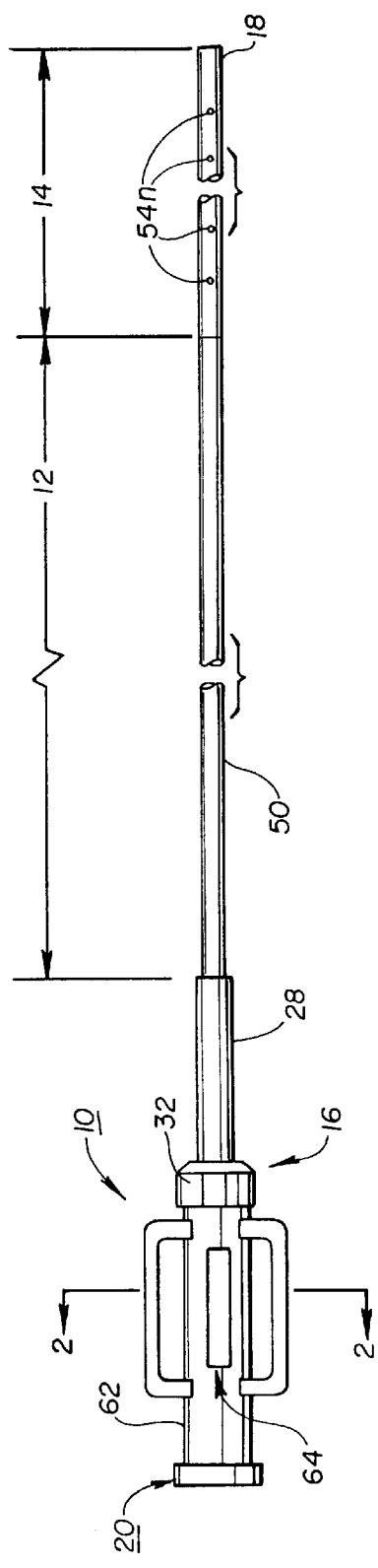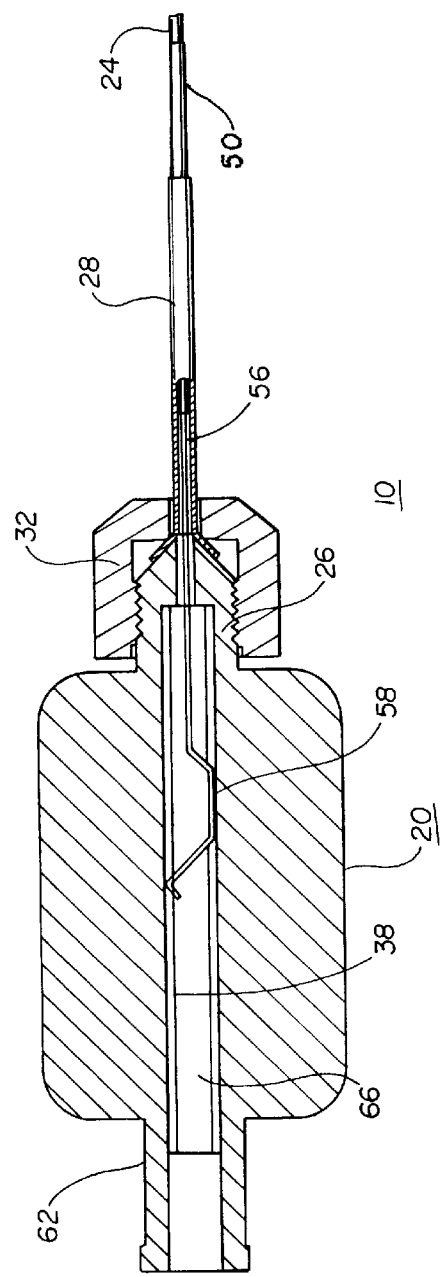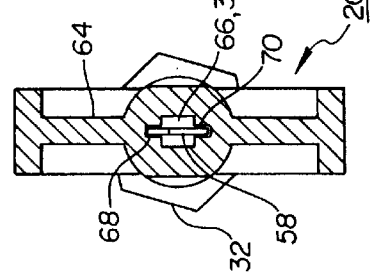

INFUSION GUIDEWIRE HAVING FIXED CORE WIRE AND FLEXIBLE RADIOPAQUE MARKER

CROSS-REFERENCE TO RELATED APPLICATION

Reference is hereby made to commonly assigned, U.S. patent application Ser. No. 08/326,609 filed Oct. 20, 1994, for INFUSION DEVICE WITH PREFORMED SHAPE in the names of George B. Wallace, et al. Now U.S. Pat. No. 5,554,114.

BACKGROUND OF THE INVENTION

1. Field of the Invention

The present invention relates to medical catheters and guidewires commonly used in the placement of catheters in a patient's vascular system, and particularly to infusion wires that can be used either as a guidewire or an infusion catheter.

2. Description of the Background Art

Medical catheters and guidewires are devices that can be navigated through narrow body passages, typically blood vessels, until the distal end section is in a desired location. Guidewires are typically used for introduction of a catheter over the guidewire.

Cardiovascular guidewires typically have a solid core wire and are dimensioned to be received within a catheter lumen as the catheter is advanced over the guidewire. One very common guidewire construction has an elongated, flexible, helical coil having a proximal end and a distal end, the latter being inserted into the patient's vascular system. The internal core wire typically extends through the coil lumen with the proximal and distal ends of the core wire attached to the proximal and distal ends of the coil. A physician controls the advancement and resulting position of the distal end of the guidewire by manipulations performed at the proximal end outside the body. Then, a catheter is advanced over the guidewire, which may be left in place or withdrawn during a procedure using the guidewire.

In order to advance the catheter over the guidewire, it must be uniform in outer diameter or have only step down diameter reductions and no diameter increases. In addition, both catheters and guidewires are preferably constructed with radiopaque markers that are have greater radiopacity and hence higher visibility under fluoroscopy than the bulk of the elongated catheter or guidewire body. These markers allow the physician to visualize the location of the distal end and/or intermediate point(s) along the elongated body within the patient's body. When both the guidewire and the catheter are provided with such markers, care must be taken that they are not so long on one or both device that they mask one another or are confusing. In this regard, it may not be desirable to make the entire wire coil in the distal segment or portion of a high density radiopaque material, because its bright appearance under fluoroscopy would mask any radiopaque marker(s) on the catheter being introduced over it.

Some guidewires are constructed of wire coil defining a guidewire lumen with an outer sheath surrounding or within the wire coil and are adapted for use both as guidewires and as infusion catheters as disclosed, for example, in U.S. Pat. Nos. 5,178,158, 5,184,627, and 5,211,636. They are provided with either a distal axial open end hole or a closed distal end with infusion side holes and a lumen for conveying infusion fluids or body fluids between the proximal end and the end hole or side holes.

In order to operate as a guide wire and be advanced through a tortuous vascular pathway to a desired infusion site, it is necessary that the overall outer diameter be as small as possible and that the construction provide for ease of advancement and excellent steerability or torqueability from the manipulated proximal end to the distal end thereof. Moreover, the construction typically requires increasing flexibility in the intermediate and distal sections. In order to provide adequate infusion capabilities, the side wall thickness has to be minimized to maximize potential infusion volume. The side wall construction also has to withstand high fluid pressures during infusion.

In use, because of the narrow gauge, flexibility and column strength, the distal portion of an infusion guidewire can be advanced to a desired site in a blood vessel. Then, the physician can advance a catheter over the infusion guidewire to the site. Depending on the design, the physician can remove the infusion guidewire from the catheter lumen or leave it in place while conducting a procedure with the catheter. Drugs or agents can be infused from the proximal end of the infusion guidewire, through the lumen, and out through the distal end lumen opening or through side holes in the sheath or through spaces between exposed turns of distal wire coil, if any, during or following the procedure using the catheter. Alternatively, distal blood pressure may be monitored through a fluid column in the lumen.

A further infusion guidewire is disclosed in U.S. Pat. No. 5,322,508 wherein a partial length core wire is attached at the distal end of a metal hypotube guidewire body and extends distally within a wire coil also attached at the distal end of the hypotube. Hypotube construction without a full length core wire may provide a maximal size cross-section, infusion lumen that may accommodate a relatively high infusion flow rate. However, the constriction at the attachment to the distal core wire extension before the distal infusion side holes negates the advantage imparted by the unobstructed hypotube lumen. Moreover, hypotube does not provide for a 1:1 torque transmission down the length of the guidewire during twisting or rotational advancement.

Currently, there are two types of clinically used infusion guidewires, one having a closed end of the type disclosed in the '627 patent and another having an open end of the type disclosed in the '158 patent and sometimes referred to as a "convertible wire". The '158 and '627 patents describe infusion wires and convertible wires having full length, coiled wire bodies within outer sheathes with constant diameter infusion lumens. In each case, the proximal sections have a polyimide tube between the wire coil and the outer sheath to strengthen that section and allow increased infusate pressure. The convertible wire disclosed in the '158 patent delivers the infusate through a distal end hole of the infusion lumen. The infusion wire disclosed in the '627 patent has a closed distal end and a plurality of infusion side holes cut in the outer sheath which covers the wire coil. In both cases, the removable core wire supplies sufficient column strength for steerability as the convertible wire or infusion wire is advanced to the treatment site.

In use of these infusion wires and convertible wires, when infusion therapy is desired, the core wire must be completely removed, since it occupies the bulk of the infusion lumen and would increase flow resistance and decrease flow rate dramatically were it left in place. The handling of this core wire is bothersome to many physicians. In addition, because of the full length coil construction (and non-attached core wire), it has no steerability or torqueability once the core wire is removed. Physicians may desire to steer the distal end into another vessel after the infusion wire is already deployed. Without the ability to steer the tip, they often will be forced to withdraw the entire convertible wire, then place a regular guidewire at the desired site, follow it with an infusion catheter advanced over the guidewire, and then remove the regular guidewire and replace it with the infusion wire.

While the '636 patent discloses an integral core wire within the infusion lumen of an infusion wire, the depicted embodiments all have at least one full length outer wire coil and a coaxial sheath leaving a small cross-section area for the infusion of infusate at slow, steady rates. A high pressure drop is effected along the length of the guidewire so that the slow infusion rate between the distal coil wire turns and the infusion pressure is relatively insensitive to the fluid pressure of the fluid entering the lumen at the proximal end.

With respect to radiopaque markers, the '627 patent depicts a typical band shaped marker that abuts the distal end of an inner sheath and lies over the continuous inner core wire. The band shaped marker causes a stiffening of the infusion wire body at that point. A further U.S. Pat. No. 4,538,622 depicts a short radiopaque coil wound into the turns of a less radiopaque guidewire coil and the use of brazing to fill the coil turns and the gap with the core wire to hold it in place. The resulting mass is stiff and causes the guidewire to be stiffer along the brazed length than adjacent proximal and distal lengths which in turn negatively affects guidewire performance.

An infusion wire with improved steerability and retaining a high infusion flow rate would therefore be a great improvement. Moreover, in infusion wires of the types described and in other guidewires and catheters, improved radiopaque markers that do not increase the outer diameter or restrict the infusion lumen would also be a great improvement.

SUMMARY OF THE INVENTION

It is therefore a principal object of the present invention to provide an infusion guidewire of minimal outer diameter having an improved steerability while maximizing the unobstructed diameter of the infusion lumen and the flow rate of infusate.

It is a further object of the present invention to provide an improved radiopaque marker or markers incorporated into a guidewire or the like that minimizes any affect on the flexibility of the guidewire body, avoids increases in the guidewire outer diameter, and does not intrude into the infusion lumen thereof.

These and other objects of the invention are realized in a flexible elongated medical infusion guidewire having proximal and distal portions between guidewire proximal and distal ends adapted for introduction through a selected path in a patient's body to a site in a blood vessel or body cavity and for infusing a drug or agent into the blood vessel or body cavity comprising: a flexible, elongated tubular, proximal inner sheath having an inner sheath lumen formed therein and a first length extending from the guidewire proximal end and distally through the proximal portion to a distal inner sheath end; a flexible, elongated, helically wound, distal wire coil having a distal coil lumen formed therein and a second length extending from the guidewire distal end and proximally through the distal portion to a proximal wire coil end thereof at a junction with the distal inner sheath end; an elongated, tubular outer sheath extending between the proximal and distal ends having an outer sheath lumen formed therein for receiving the proximal inner sheath in a proximal segment thereof and the distal wire coil in a distal segment thereof such that the inner sheath lumen and the distal coil lumen are substantially co-axially aligned at the junction thereof and define an infusion lumen having an infusion diameter, the outer sheath having at least one infusion port formed therein in the distal segment thereof for allowing transmission of fluids between the infusion lumen, adjacent turns of the distal wire coil and the infusion port to the exterior of the distal segment of the outer sheath; an elongated stiffening core wire having a proximal core wire end and a distal core wire end and an outer diameter smaller than the infusion diameter positioned within the infusion lumen to extend therein from the proximal end to the distal end of the outer sheath; means for attaching the distal core wire end to the distal end of the distal wire coil within the outer sheath; and means for attaching the proximal core wire end to the proximal ends of the outer and inner tubular sheaths.

The infusion guidewire of the present invention provides enhanced handling advantages and infusate flow rates equal to or exceeding conventional infusion wires or convertible wires, while retaining the core wire in place. This allows the physician to avoid removing and replacing the infusion guidewire with a regular guidewire as described above.

In infusion guidewires of the type having a distal wire coil, a radiopaque marker may be disposed in accordance with a further aspect of the present invention in coaxial alignment with the inner tubular sheath and the distal wire coil within the outer sheath lumen. Preferably, the distal wire coil is formed with at least a plurality of spacings between adjacent coil turns thereof in at least a portion adjacent to the proximal wire coil end thereof, and the radiopaque means comprises a radiopaque wire coil having a plurality of coil turns and a further inner coil lumen formed therein, the plurality of coil turns disposed within a like plurality of the spacings between adjacent distal wire coil turns such that the distal coil lumen and the further coil lumen are substantially co-axially aligned with the infusion lumen.

The coiled wire radiopaque marker is maintained in coaxial alignment with the distal wire coil by pressure applied by the inner sheath and maintained in longitudinal alignment with the distal wire coil and the inner sheath by the outer sheath. The absence of solder or joint adhesive allows the coiled wire radiopaque marker, and the entire infusion guidewire, to flex where it is intertwined with the distal wire coil.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 1 is a plan view of an infusion wire according to one embodiment of the present invention;

FIG. 2 is an end view of the proximal end cross-section of the infusion wire of FIG. 1;

FIG. 3 is an end cross-section view of the proximal end of the infusion wire of FIG. 1;

DETAILED DESCRIPTION OF THE PREFERRED EMBODIMENTS

Figure 4:
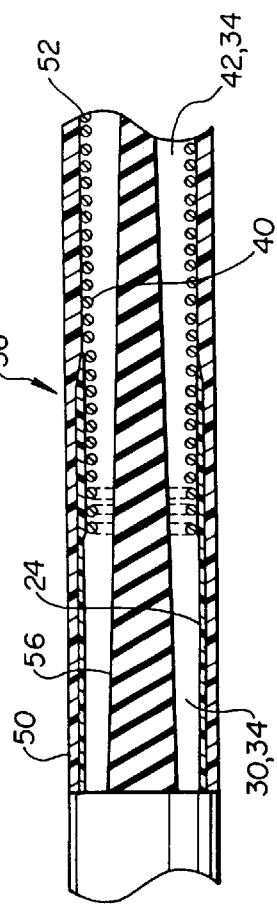
FIG. 4 is a partial cross-section plan view of an intermediate segment of the infusion wire of FIG. 1.

Turning now to FIGS. 1–5, they depict the construction of an infusion guidewire 10 in accordance with the preferred embodiment of the present invention incorporating the inventive infusion guidewire construction. The flexible elongated medical infusion guidewire 10 has proximal portion 12 and distal portion 14 between guidewire proximal end 16 and distal end 18 adapted for introduction through a selected path in a patient's body to a site in a blood vessel or body cavity and for infusing a drug or agent into the blood vessel or body cavity. Preferably, the overall usable length of the infusion guidewire 10 is on the order of 145 cm and an outer diameter of about 0.035 inches. The distal portion 14 preferably ranges from about 3.0 cm to about 20.0 cm.

As shown in FIGS. 1–3, the proximal portion 12 includes the luer connector housing 20 and the flexible, elongated, tubular, proximal inner sheath 24 of a first length extending from the guidewire proximal end 16 and distally through the proximal portion 12 having an inner sheath lumen 30 formed thereby. The inner sheath 24 is preferably composed of a high strength, thin walled tubing, preferably polyimide, of 0.0295 inches in outer diameter and 0.0275 inches inner diameter, for example, that defines an inner sheath lumen 30 therein. The proximal end of the polyimide inner sheath 24 is sealed within the lumen at one end of a strain relief 28 which is flared and compression fit at its other end between the male connector fitting 26 and a threaded female connector nut 32 threaded over it.

The polyimide inner sheath 24 extends distally through the proximal portion 12 to junction 36 with a proximal end of a flexible, elongated, helically wound, distal wire coil 40 of a second length extending to a distal wire coil end thereof at the guidewire distal end 18. The wire coil 40 preferably is formed of circular cross-section stainless steel wire of about 0.004 inches diameter wound into a wire coil having an inner diameter of about 0.021 inches defining a wire coil infusion lumen 42 and an outer diameter of about 0.029 inches. As shown in FIG. 4, the proximal end of the wire coil 40 is forced into the distal end inner sheath lumen 30 of the polyimide sheath 24.

Returning to FIG. 1, an elongated, tubular outer sheath 50 extends through the proximal and distal portions 12, 14 having an outer sheath lumen 52 formed therein for receiving the proximal inner sheath 24 in a proximal portion thereof and the distal wire coil 40 in a distal portion thereof. The inner sheath lumen 30 and the distal wire coil lumen 42 are substantially co-axially aligned at their junction 36 and define an infusion lumen 34 having an infusion diameter that is stepped down slightly through and distally to junction 36. The outer sheath 50 provides a substantially constant outer diameter through the length of the infusion guidewire. The outer sheath 50 has at least one infusion port $54_n$ formed therein in the distal portion thereof for allowing transmission of fluids between the infusion lumen, adjacent enclosed turns of the distal wire coil 40 and the infusion port(s) $54_n$ to the exterior of the distal portion of the outer sheath 50.

In order to allow the passage of infusate between the inner infusion lumen and the infusion port(s), the adjacent turns of the distal wire coil 40 are separated by approximately one-half of wire diameter or about 0.002 inches. Preferably, the number n and the spacings apart of the infusion ports $54_n$ may be selected as a function of the length of distal portion 14. For example, the number n=8 for 3.0 cm length, n=14 for 6.0 cm, n=20 for 9.0 cm, and n=26 for 12.0 cm.

The outer sheath 50 is preferably a Teflon® (PTFE) shrink tube that can then be shrunken over the entire assembly of the inner polyimide sheath 24 and the distal wire coil 40 to lock the assembly in place and provide a lubricous outer surface. Prior to applying heat, the side holes or infusion ports $54_n$ are cut in or formed in the distal portion of the tube that will be shrunk over the separated turns of distal wire coil 40. At the polyimide inner sheath 24/wire coil 40 junction 36, the shrunken outer sheath 50 locks the assembly together with without the need for adhesives, braze, solder or the like, creating a flexible zone of junction 36.

Figure 5:
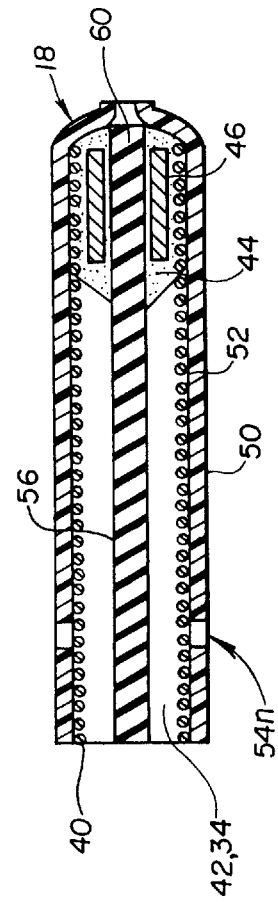
FIG. 5 is a partial cross-section plan view of the distal end segment of the infusion wire of FIG. 1.

An elongated stiffening core wire 56 having a proximal core wire end 58 and a distal core wire end 60 and an outer diameter smaller than the infusion diameter of the infusion lumen is also depicted in FIGS. 3–5. The stiffening core wire 56 is positioned within the aligned axial lumens 30 and 42 to extend between the proximal and distal ends 16, 18 of the guide wire 10. The integral stiffening core wire 56 preferably consists of a 0.016 inch diameter, stainless steel core wire which tapers to 0.0065 inches at the distal end 18. A continuous taper is commenced just proximal to the junction of inner polyimide sheath 24 and distal wire coil 40. Ideally, the 0.009" diameter portion of the taper is located at the most proximal portion end of the distal wire coil 40. The tapering provides a relatively constant cross-section area infusate passageway within the infusion lumen not occupied by the core wire 56, despite narrowing of the infusion lumen at and distally to the junction 36.

The integral core wire 56 is brazed at its distal core wire end 60 to the distal end of the distal wire coil 40 forming a braze ball 44 as shown in FIG. 5. The brazing creates the integral attachment of the core wire end 60 that provides for increased steerability and torque transfer. The core wire distal end 60 may be flattened prior to brazing in order to create a mechanical lock for a stronger braze pull force. The distal core wire end 60 and distal wire coil 40 can also be soldered or welded or attached with adhesive, but brazing is preferred. A platinum marker tube 46 made from a short length of platinum tubing is encapsulated in the braze ball 44 (or other attachment means) between the core wire 56 and the distal wire coil 40.

The braze ball 44 also serves to close the distal end of the infusion wire to internal infusate pressure. This is effected when the outer sheath 50 is heat shrunk. The tip of the heat shrink tube sheath 50 is shrunk past the braze ball 44 to lock it in, and any remaining distal tail is trimmed short to about 0.015 inches in length.

The proximal end of core wire 56 is attached to the proximal luer connector housing 20 and thereby to the proximal ends of the inner and outer tubular sheaths 24 and 50. The attachment is in such a way that by torquing the connector housing 20, the distal core wire end 60 (and the distal end 18 of the guide wire 10) can be steered.

As shown in FIG. 3, the proximal core wire end 58 is bent into a shape which fits into a keyed groove 38 inside the connector housing 20. The connector housing 20 includes a hub member 62 having an outer surface 64 adapted to be manually engaged and manipulated to advance and rotate infusion guidewire 10 through a blood vessel. The hub member 62 has an internal conduit 66 therein for transmission of infusion fluids to the infusion lumen 34 and for receiving the proximal core wire end 58. The proximal core wire end 58 is formed with a laterally bent shape in one plane of a size to prevent the bent shape from being advanced distally through the conduit 66 and the aligned infusion lumen 34 and for fixing the core wire 56 from rotation in the conduit 66 and the infusion lumen 34 during advancement and rotation of the infusion guidewire 10. A pair of planar side walls 68, 70 extend laterally on either side from the conduit 66 within the hub member 62 to form the cavity of the keyed groove 38 for receiving the bent shape of the proximal core wire end 58 and for restraining rotation thereof. The bent shape, proximal core wire end 58 can alternatively be insert molded into the proximal connector housing 20, leaving the conduit 66 open.

Rotational motion imparted to the hub member outer surface 64 is imparted to the core wire 56 and through the core wire 56 to the braze ball 44 attaching the distal core wire end 60 to the distal end of the distal wire coil 40 within the outer sheath 50. Because the distal end of the core wire 56 is brazed to the distal end of distal wire coil 40, the guidewire distal end 18 will be steerable. The core wire 56 can be shaped at the guidewire distal end 18 by the physician to improve the steerability.

The tapered core wire 56 within the infusion lumen 34 of the aligned proximal inner sheath and the distal wire coil an the integral attachment of its proximal and distal ends 58, 60 as described above replaces the full length wire coils of.the side hole infusing guidewires of the above-referenced '627, and '636 patents. The resulting net cross-section area provides a flow lumen within the same outer diameter that allows a flow rate exceeding or comparable to the flow rates of the side hole infusing guidewires of the '636 and '627 patents, respectively. For example, the flow rates for room temperature water at 100 psi are specified for the following differing infusate lengths:

3.0 cm 28 cc/min 6.0 cm 30 cc/min 9.0 cm 32 cc/min 12.0 cm 34 cc/min

In use of the guidewire 10, both slow drip, i.e., weeping, infusion and spray infusion may be effected. The guidewire 10 is further specified to withstand pressures of up to 350 psi without bursting or tip leakage.

Turning to a further aspect of the present invention, current infusion guidewires (and other similar catheters) make use of high radiopacity radiopaque marker bands which are placed over a stainless steel coil or tubular sheath or the like and surrounded by PTFE shrink tubing. Alternatively, the marker bands are adhered, welded or brazed in line with a side wall coil or sheath or inside the lumen thereof. This layering procedure causes an increase in stiffness at the junction and either an increase in total outer diameter, or a decrease in inner lumen diameter.

Figure 6:
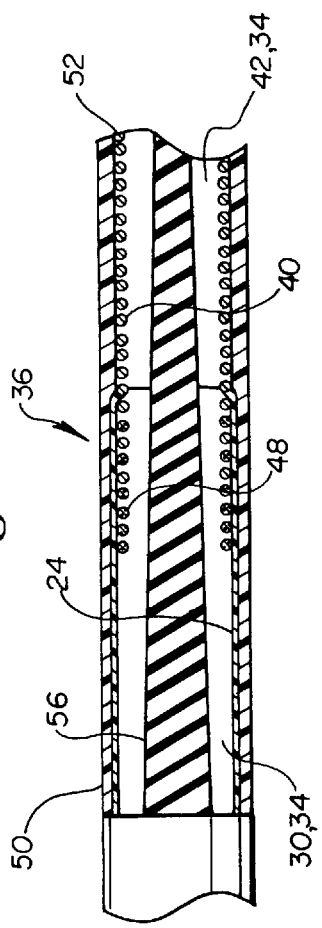
FIG. 6 is a partial cross-section plan view of a variation of the intermediate segment of the infusion wire of FIG. 1 including an integral radiopaque marker in accordance with a further aspect of the invention.

In accordance with this aspect of the invention, as shown in FIG. 6, platinum spring marker wire coil 48, preferably made in the same 0.004 inch wire diameter and coiled with the same pitch, inside diameter and outside diameter as the distal wire coil 40, is screwed into the turns of the distal wire coil 40. The wire coils 40 and 48 are both wound in the same direction preferably with a gap of one-quarter to one times wire diameter. This allows the two coils to be screwed together preferably over a close fitting mandrel. The platinum marker wire coil 48 can be short (e.g. 0.050" long), and the coil turns need only to be wound together a few times to provide a good lock.

The two wire coils 48 and 40 are screwed together to form a high radiopacity marker of about 0.075 inches long. Both ends of the platinum marker wire coil 48 and a number of turns of the proximal end of the stainless steel distal wire coil 40 are forced into an interference fit within the distal end opening of inner sheath lumen 30. The inner sheath lumen 30 protects and holds the ends of the wire coil 48 turns from moving laterally, and maintains the diameter of the distal wire coil lumen 42 constant, and the outer sheath 50 prevents longitudinal displacement or separation of the intertwined coil turns from the inner sheath lumen 30 without requiring an adhesive braze or solder. The platinum wire coil 48 turns at the proximal end of the stainless distal wire coil 40 thereby serve as a radiopaque marker to mark the proximal end of the infusion section.

As noted above, this aspect of the invention may alternatively be incorporated into other known constructions of guidewires, infusion wires, convertible wires and catheters in substitution for the conventional radiopaque markers. Because the platinum wire coil is wound in an intertwined manner with the stainless wire coil, there is no reduction of a lumen diameter or increase in the outer diameter at the marker section. The resulting joint provides a radiopaque marker that can be readily seen under fluoroscopy, yet which maintains the identical inner and outer diameter as a less radiopaque stainless steel coil and virtually the same flexibility without a marker. The resulting product has an outer surface with no bumps or increases in diameter and an inner lumen with no added restrictions to flow or to tracking over a guide wire.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

PARTS LIST FOR FIGS. 1–6 infusion guidewire 10
proximal portion 12
distal portion 14
guidewire proximal end 16
guidewire distal end 18
luer connector housing 20
proximal inner sheath 24
threaded male connector fitting 26
strain relief tube 28
inner sheath lumen 30
threaded female connector nut 32
infusion lumen 34
junction 36
keyed groove 38
distal wire coil 40
distal wire coil lumen 42
braze ball 44
platinum marker tube 46
platinum marker wire coil 48
tubular outer sheath 50
outer sheath lumen 52
infusion port $54_n$
elongated stiffening core wire 56
proximal core wire end 58
distal core wire end 60
hub member 62
outer surface 64
internal conduit 66
planar side walls 68, 70

What is claimed is:

1. A flexible elongated medical infusion guidewire having guidewire proximal and distal portions enclosing an infusion lumen and extending between proximal and distal guidewire ends, the guidewire adapted to be introduced through a selected path in a patient's body to a site in a blood vessel or body cavity for infusing a drug or agent through the infusion lumen and into the blood vessel or body cavity, the infusion guidewire further comprising:

an elongated, tubular outer sheath of substantially constant outer diameter having an outer sheath lumen formed therein extending between said guidewire proximal and distal ends, said outer sheath having a plurality of infusion ports formed through the outer sheath side wall and distributed along an infusate length of said guidewire distal portion;

a flexible, elongated, tubular, proximal inner sheath having an inner sheath lumen formed therein and having an inner sheath lumen diameter and an inner sheath lumen length, said inner sheath disposed within said outer sheath lumen and extending from said guidewire proximal end and distally through said guidewire proximal portion to a distal inner sheath end, said inner sheath lumen defining said infusion lumen through said guidewire proximal portion;

an elongated, helically wound, distal wire coil having a distal wire coil lumen formed therein and having a distal wire coil inner diameter and distal wire coil length, said distal wire coil disposed within said outer sheath lumen and extending from a distal wire coil distal end at said guidewire distal end and proximally through said guidewire distal portion and terminating at a distal wire coil proximal end thereof at a junction with said distal inner sheath end, said distal wire coil lumen axially aligned with said inner sheath lumen at said junction by said tubular outer sheath and defining said infusion lumen through said guidewire distal portion, said distal wire coil having spaced apart wire coil turns defining an elongated helical spacing along said infusate length of said guidewire distal portion;

an elongated stiffening core wire having a proximal core wire end and a distal core wire end positioned within said infusion lumen to extend therein from said guidewire proximal end to said guidewire distal end, said core wire having a proximal core wire section with a proximal core wire diameter smaller than said inner sheath lumen diameter in said guidewire proximal portion, a distal core wire section with a distal core wire diameter smaller than said proximal core wire diameter in said guidewire distal portion and an intermediate core wire section having a tapered core wire diameter that decreases from said proximal core wire diameter to said distal core wire diameter;

means for attaching said distal core wire end to said distal wire coil end; and a hub formed at the guidewire proximal end for infusing fluids into said infusion lumen and for coupling said proximal core wire end to said proximal ends of said outer and inner tubular sheaths and disposed within said infusion lumen for minimally obstructing said infusion lumen through the length of said infusion lumen, whereby fluids infused into said hub under pressure flow through said infusion lumen alongside said core wire, through the elongated helical spacing between the wire coil turns, and through the plurality of infusion ports to infuse the fluid into the blood vessel or body cavity exterior of said outer sheath distal portion along said infusate length thereof.

2. The infusion guidewire of claim 1 further comprising:

radiopaque means disposed in coaxial alignment with said inner tubular sheath and said distal wire coil within said outer sheath lumen.

3. The infusion guidewire of claim 2 wherein:

said radiopaque means comprises a radiopaque wire coil formed of a radiopaque material having a plurality of spaced apart radiopagque wire coil turns and a radiopaque coil lumen formed therein, said plurality of radiopaque wire coil turns intertwined in the helical spacing between a like plurality of adjacent distal wire coil turns and maintained in coaxial alignment therewith such that said distal coil lumen and said radiopaque coil lumen are substantially co-axially aligned with said infusion lumen.

4. The infusion guidewire of claim 2 wherein:

said means for attaching said distal core wire end to said distal wire coil distal end is at least partially within said outer sheath and comprises a closed end, ball braze.

5. The infusion guidewire of claim 4 wherein said hub further comprises:

a hub member having an outer surface adapted to be engaged to advance and rotate said infusion guidewire through a blood vessel and a conduit therein for transmission of infusion fluids to said infusion lumen and for receiving said proximal core wire end;

core wire fixation means formed in said conduit for fixing said proximal core wire end from rotation in said conduit and in said infusion lumen during advancement and rotation of said infusion guidewire.

6. The infusion guidewire of claim 5 wherein:

said core wire is formed with a bent shape in one plane at said proximal core wire end of a size to prevent said bent shape of said core wire from being advanced distally through said conduit and said aligned infusion lumen; and said core wire fixation means further comprises a pair of planar side walls extending from said conduit within said hub member to form a cavity for receiving said bent shape of said core wire and for restraining rotation thereof, whereby rotational motion imparted on said hub member is imparted to said core wire and through said core wire to said means for attaching said distal core wire end to said distal wire coil distal end within said outer sheath.

7. The infusion guidewire of claim 1 wherein:

said means for attaching said distal core wire end to said distal wire coil distal end within said outer sheath comprises a closed end, ball braze.

8. The infusion guidewire of claim 7 wherein said hub further comprises:

a hub member having an outer surface adapted to be engaged to advance and rotate said infusion guidewire through a blood vessel and a conduit therein for transmission of infusion fluids to said infusion lumen and for receiving said proximal core wire end;

core wire fixation means formed in said conduit for fixing said proximal core wire end from rotation in said conduit and said infusion lumen during advancement and rotation of said infusion guidewire.

9. The infusion guidewire of claim 8 wherein:

said core wire is formed with a bent shape in one plane at said proximal core wire end of a size to prevent said bent shape of said core wire from being advanced distally through said conduit and said aligned infusion lumen; and said core wire fixation means further comprises a pair of planar side walls extending from said conduit within said hub member to form a cavity for receiving said bent shape of said core wire and for restraining rotation thereof, whereby rotational motion imparted on said hub member is imparted to said core wire and through said core wire to said means for attaching said distal core wire end to said distal end of said distal wire coil within said outer sheath.

10. The infusion guidewire of claim 1 wherein said hub further comprises:

a hub member having an outer surface adapted to be engaged to advance and rotate said infusion guidewire through a blood vessel and a conduit therein for transmission of infusion fluids to said infusion lumen and for receiving said proximal core wire end;

core wire fixation means formed in said conduit for fixing said proximal core wire end from rotation in said conduit and said infusion lumen during advancement and rotation of said infusion guidewire.

11. The infusion guidewire of claim 10 wherein:

said core wire is formed with a bent shape in one plane at said proximal core wire end of a size to prevent said bent shape of said core wire from being advanced distally through said conduit and said aligned infusion lumen; and said core wire fixation means further comprises a pair of planar side walls extending from said conduit within said hub member to form a cavity for receiving said bent shape of said core wire and for restraining rotation thereof, whereby rotational motion imparted on said hub member is imparted to said core wire and through said core wire to said means for attaching said distal core wire end to said distal wire coil distal end within said outer sheath.

12. The infusion guidewire of claim 14 wherein said distal and radiopaque wire coils are wound in wire coil turns having substantially the same outer coil diameter and inner coil diameter.

13. The infusion guidewire of claim 12 wherein said outer sheath lumen contacts and aligns the outer diameters of said distal and radiopaque wire coils and applies compressive force thereto.

14. A flexible elongated medical infusion guidewire having guidewire proximal and distal portions enclosing an infusion lumen and extending between proximal and distal guidewire ends, the guidewire adapted to be introduced through a selected path in a patient's body to a site in a blood vessel or body cavity for infusing a drug or agent through the infusion lumen and into the blood vessel or body cavity, the infusion guidewire further comprising:

an elongated, tubular outer sheath of substantially constant outer diameter having an outer sheath lumen formed therein extending between said guidewire proximal and distal ends, said outer sheath having at least one infusion port formed through the outer sheath side wall in an infusate length of said guidewire distal portion;

an elongated, tubular, proximal inner sheath having an inner sheath lumen formed therein and having an inner sheath lumen diameter and an inner sheath lumen length, said inner sheath disposed within said outer sheath lumen and extending from said guidewire proximal end and distally through said guidewire proximal portion to a distal inner sheath end, said inner sheath lumen defining said infusion lumen through said guidewire proximal portion;

a flexible, elongated, helically wound, distal wire coil having a distal wire coil lumen formed therein and having a distal wire coil inner diameter and distal wire coil length, said distal wire coil disposed within said outer sheath lumen and extending from a distal wire coil distal end at said guidewire distal end and proximally through said guidewire distal portion and terminating at a distal wire coil proximal end thereof at a junction with said distal inner sheath end, said distal wire coil lumen axially aligned with said inner sheath lumen at said junction by said tubular outer sheath, said distal wire coil having spaced apart wire coil turns defining an elongated helical spacing along said infusate length of said guidewire distal portion;

a radiopaque wire coil formed of a radiopaque material having a plurality of spaced apart radiopaque wire coil turns and a radiopaque coil lumen formed therein, said plurality of radiopaque wire coil turns intertwined in the helical spacing between a like plurality of adjacent distal wire coil turns and maintained in coaxial alignment therewith such that said distal coil lumen and said radiopaque coil lumen are substantially co-axially aligned with and define said infusion lumen through said guidewire distal portion;

an elongated stiffening core wire having a proximal core wire end and a distal core wire end positioned within said infusion lumen to extend therein from said guidewire proximal end to said guidewire distal end;

means for attaching said distal core wire end to said distal wire coil distal end; and a hub formed at the guidewire proximal end for infusing fluids into said infusion lumen and for coupling said proximal core wire end to said proximal ends of said outer and inner tubular sheaths and disposed within said infusion lumen for minimally obstructing said infusion lumen through the length of said infusion lumen, whereby fluids infused into said hub under pressure flow through said infusion lumen alongside said core wire, through the elongated helical spacing between the wire coil turns, and through the plurality of infusion ports to infuse the fluid into the blood vessel or body cavity exterior of said outer sheath distal portion along said infusate length thereof.

15. The infusion guidewire of claim 14 wherein said radiopaque wire coil extends from said junction and said distal wire coil proximal end through a proximal section of said distal wire coil and terminates proximally to said distal coil wire distal end.

* * * * *